United States Patent [19]

Smith et al.

[11] Patent Number: 5,254,735
[45] Date of Patent: Oct. 19, 1993

[54] PROCESS FOR PREPARING SOLID AMINE OXIDES

[75] Inventors: Kim R. Smith; Y.-D. Mark Chen; Rebecca F. Smith; James E. Borland; Joe D. Sauer, all of Baton Rouge, La.

[73] Assignee: Ethyl Corporation, Richmond, Va.

[21] Appl. No.: 878,265

[22] Filed: May 4, 1992

Related U.S. Application Data

[63] Continuation-in-part of Ser. No. 724,127, Jul. 1, 1991, abandoned, which is a continuation-in-part of Ser. No. 652,618, Feb. 8, 1991, abandoned.

[51] Int. Cl.⁵ ............................................. C07C 291/00
[52] U.S. Cl. ..................................... 564/298; 564/297
[58] Field of Search ....................... 564/297, 298, 299

[56] References Cited

U.S. PATENT DOCUMENTS

| 4,247,480 | 1/1981 | Murata et al. | 564/298 |
| 4,748,275 | 5/1988 | Smith et al. | 564/298 |

FOREIGN PATENT DOCUMENTS 0307184  3/1989  European Pat. Off.

Primary Examiner—Glennon H. Hollrah
Assistant Examiner—Shailendra Kumar
Attorney, Agent, or Firm—Patricia J. Hogan

[57] ABSTRACT

A solid amine oxide is prepared by reacting a tert-amine with at least a stoichiometric amount of an aqueous hydrogen peroxide having a concentration of at least 50% by weight in the presence as the reaction medium of a normally gaseous material which (a) has a critical temperature <160° C. and a critical pressure <12 MPa, (b) is in a liquefied, densified, or supercritical state in which it has a density of at least 0.1 g/cc, and (c) is present in an amount sufficient to maintain the reaction mixture stirrable throughout the reaction.

17 Claims, No Drawings

PROCESS FOR PREPARING SOLID AMINE OXIDES

CROSS-REFERENCE TO RELATED APPLICATION

This application is a continuation-in-part of copending application Ser. No. 724,127, filed Jul. 1, 1991 now abandoned, which in turn is continuation-in-part of Ser. No. 652,618, filed Feb. 8, 1991, abandoned.

FIELD OF INVENTION

The invention relates to a process for preparing solid amine oxides.

BACKGROUND

It is known that amine oxides are useful materials, those that are most attractive commerically being the mixed amine oxides, i.e., amine oxides having at least one long-chain group and at least one short-chain group attached to the amino nitrogen. These oxides are used in many formulations in which their surface activity is an attribute, e.g., laundry detergents, rinses, and dryer sheets; shampoos and hair conditioners; soaps, and other personal hygiene products.

As taught in U.S. Pat. No. 4,748,275 (Smith et al.-I) and the references discussed therein, there are many known methods of preparing amine oxides by reacting tert-amines with aqueous hydrogen peroxide. The syntheses most commonly employed are the aqueous processes utilizing sufficient water to provide the products as aqueous solutions, e.g., the processes of U.S. Pat. No. 4,247,480 (Murata et al.) and European Patent Application 0307184 (Bauer et al.) in which carbon dioxide is used to promote the reaction. Less commonly, the amine oxides are prepared in organic solvents, as in U.S. Pat. No. 3,776,959 (Stalioraitis et al.).

The aforementioned solvent processes are quite satisfactory for the products which are to be used in applications in which their water or organic solvent content can be tolerated. However, the utilization of these processes necessitates the performance of after-treatments, such as spray-drying or evaporation, when the amine oxides are intended for use in applications, such as dry solid laundry detergent formulations, in which the presence of the solvent cannot be tolerated.

Smith et al.-I teach that the use of a temperature high enough to maintain the product in a molten state permits some amine oxides to be prepared in the solid form that makes them more desirable than the dissolved oxides for some purposes.

Copending application Ser. No. 07/591,426 (Smith et al.-II) discloses a process in which stirrability of the reaction mixture is maintained by conducting at least the latter part of the tert-amine/hydrogen peroxide reaction in an organic solvent in which the amine and amine oxide are soluble at the reaction temperatures but in which the amine oxide is insoluble at a lower temperature, thus permitting a relatively easy recovery of the amine oxide in solid form. In some respects this process is more attractive than the process of Smith et al.-I. However, when it is used to prepare a substantially pure amine oxide, it requires the use of centrifugation, crystallization, and drying steps which add to its cost.

SUMMARY OF INVENTION

It has now been found that amine oxides can be more economically prepared in solid form by reacting a tert-amine with at least a stoichometric amount of an aqueous hydrogen peroxide having a concentration of at least 50% by weight in the presence as the reaction medium of a normally gaseous material which (a) has a critical temperature < 160° C. and a critical pressure < 12 MPa, (b) is in a liquefied, densified, or supercritical state in which it has a density of at least 0.1 g/cc, and (c) is present in an amount sufficient to maintain the reaction mixture stirrable throughout the reaction.

DETAILED DESCRIPTION

The process of the invention is applicable to the oxidation of any tert-amine which can be reacted with hydrogen peroxide to form an amine oxide. As is known, these amines include a variety of tert-amines corresponding to the formula RR'R"N wherein R, R', and R" are independently selected from alkyl, hydroxyalkyl, cycloalkyl, and aralkyl groups containing up to 30 carbons and any two of those groups may form a non-aromatic heterocyclic group, such as a morpholine or piperidine ring, with the nitrogen. However, they are generally tert-amines of that formula in which R, R', and R" are independently selected from primary alkyl and hydroxyalkyl groups containing 1–30 carbons.

Because of greater interest in the oxides prepared from them, the tert-amines which are apt to be preferred for use in the process are those in which R is methyl, ethyl, or hydroxyethyl; R' is a primary alkyl group containing 6–24 carbons; and R" is independently selected from methyl, ethyl, hydroxyethyl, and primary alkyl groups containing 6–24 carbons. Of these preferred tert-amines, those which are particularly preferred are those in which the primary alkyl groups have a straight chain in at least most of the molecules, generally at least 70%, preferably at least 90% of the molecules.

Exemplary of the tert-amines that may be used are trimethylamine, triethylamine, N-isobutyldimethylamine, trihexylamine, N,N-dimethyl-2-ethylhexylamine, N-eicosyldimethylamine, N-isobutyl-N-triacontylmethylamine, N-benzyldimethylamine, N-ethyldibenzylamine, N,N-diisobutyl-4-t-butylbenzylamine, tri-2-hydroxyethylamine, and, more preferably, (1) the N-alkyldimethyl-and N,N-dialkylmethylamines in which the alkyl groups are hexyl, octyl, decyl, dodecyl, tetradecyl, hexadecyl, octadecyl, eicosyl, docosyl, and/or tetracosyl, (2) the corresponding amines in which the methyl groups are replaced with ethyl or hydroxyethyl groups, and (3) mixtures of such amines.

The aqueous hydrogen peroxide employed in the reaction may be any aqueous hydrogen peroxide having a concentration of at least 50% by weight. However, to minimize the amount of water in the product, it is preferred to use a hydrogen peroxide having a concentration of at least about 70%, generally about 70–90% by weight.

As is customary in oxidations of tert-amines, the amount of hydrogen peroxide utilized is at least the stoichiometric amount. It is undesirable, however, to use too great an excess of the oxidizing agent, so the amount employed is generally about 1.1–1.2 times the stoichiometric amount.

The fluid used as the reaction medium for the process may be a liquefied, densified, or supercritical form of any normally gaseous material which has a critical temperature < 160° C. and a critical pressure < 12 MPa; has a density of at least 0.1 g/cc, preferably at least 0.15 g/cc, and more preferably at least 0.2 g/cc under the reaction conditions; and is inert in the sense that it will neither prevent the reaction from occurring nor react with the product. Such normally gaseous materials include, e.g., air, oxygen, carbon dioxide, nitrogen, argon, ethylene, methane, ethane, propane, butane, isobutane, methyl fluoride, trifluoromethane, tetrafluoromethane, chlorotrifluoromethane, and mixtures thereof, as well as the other suitable gases mentioned in Lange, *Handbook of Chemistry*, Ninth Edition, McGraw-Hill Book Company, Inc. (New York), 1956, pp. 1494–1498, the teachings of which are incorporated herein by reference.

For economic reasons, it is frequently preferred that the reaction medium be one formed from a normally gaseous material which has a critical temperature that is above or not much below room temperature, generally a critical temperature of at least 0° C., preferably at least 20° C., most preferably 20°–50° C., e.g., materials such as ethylene, carbon dioxide, chlorotrifluoromethane, methyl fluoride, trifluoromethane, ethane, propane, butane, and isobutane.

Liquefied, densified, or supercritical carbon dioxide is generally the most preferred reaction medium because of its being able to serve the additional function of promoting the reaction, and a medium formed from air can also speed the reaction. However, any of the other media of the invention can be employed when increasing the rate of the reaction is not a prime consideration.

Most commonly, the medium which is employed is one that is commercially available as a liquefied gas and can simply be introduced into the reaction vessel in liquid form and maintained in liquid form by the use of pressure. However, if desired, it may be acquired in the gaseous state and introduced into the reaction vessel via a compressor to convert it to a liquefied, densified, or supercritical state.

The manner in which the process is conducted can be varied considerably as long as at least the latter part of the reaction is conducted in an amount of the reaction medium sufficient to maintain the reaction mixture stirrable throughout the reaction. The process may be a batch, semi-batch, or continuous process; and the reaction medium may be present throughout the reaction, or it may be added to the reaction mixture only when the reaction has proceeded to the stage where a solvent is needed to maintain the reaction mixture stirrable. Also, the ingredients of the reaction mixture can be combined in many different ways. For example:

(1) the hydrogen peroxide can be gradually added to a solution of the tert-amine in the reaction medium, (2) separate streams of the tert-amine and the hydrogen peroxide can be gradually added to the reaction medium, (3) separate streams of the hydrogen peroxide and the reaction medium can be gradually added to the tert-amine, or (4) the hydrogen peroxide can be gradually added to the tert-amine and allowed to react therewith until a substantial amount of amine oxide has been formed before the reaction medium is added.

As in conventional processes, it is preferred to combine the reactants at a controlled rate because of the exothermic nature of the reaction; the reaction may be conducted in the presence of a chelating agent, such as diethylenetriaminepentaacetic acid or ethylenediaminetetraacetic acid, if desired; and it is generally preferred to maintain contact between the reactants until the reaction is substantially complete.

When the reaction medium is not added until needed, the temperatures at which the reaction may be conducted during the earlier portion of the reaction may be any temperatures conventionally employed for such reactions, usually temperatures in the range of 20°–90° C.

It is sometimes desirable to continue using such temperatures after the reaction medium is added when they are appropriate for maintaining the reaction medium in the desired liquefied gas, densified gas, or supercritical fluid state. However, even when the temperatures would be appropriate for the portion of the reaction conducted in the reaction medium, it can sometimes be desirable to use a lower temperature for the latter part of the reaction, e.g., when that portion of the reaction is conducted in the presence of liquefied, densified, or supercritical carbon dioxide.

When the reaction medium is such a carbon dioxide, the reaction proceeds much more rapidly than conventional carbon dioxide-promoted amine oxide syntheses because of the larger amounts of carbon dioxide used as a solvent, thus permitting lower temperatures to be used without slowing the reaction to a commercially-unacceptable rate. Accordingly, it could be desirable to lower the temperature from one in an upper portion of the 20°–90° C. range to a lower temperature in that range or to a temperature even below 20° C. for the portion of the reaction during which the reaction medium is present.

The temperature and pressure conditions employed for the reaction while the reaction medium is present will vary with the particular reaction medium used. Thus, e.g., (1) a temperature and pressure below the critical temperature and critical pressure of the normally gaseous material are used when it is desired to maintain the reaction medium as a liquefied gas, (2) a temperature and pressure above the critical temperature but below the critical pressure are utilized when the reaction medium is to be maintained as a densified gas, (3) temperatures and pressures above the critical temperature and pressure are used when the reaction medium is to be a supercritical fluid, (4) and variations among those conditions are permitted when it is wished to change the reaction medium from being in one of the acceptable fluid states (i.e., liquefied gas, densified gas, and supercritical fluid) to another of those states during the course of the reaction. The temperatures and pressures which can be used to maintain the utilizable normally gaseous materials in these states are, of course, already known to those skilled in the art.

In the preferred embodiment of the invention wherein the reaction medium is liquefied carbon dioxide, the reaction may be virtually instantaneous at room temperature and the pressure required to keep the carbon dioxide liquid. It could therefore be desirable to conduct the entire reaction at room temperature when the liquefied carbon dioxide is present throughout the reaction, although higher temperatures are preferably used for any portion of the reaction conducted before the liquefied carbon dioxide is added, and higher temperatures could also be used after the addition of the liquefied carbon dioxide when it is desired to convert the liquefied carbon dioxide to densified or supercritical carbon dioxide during the reaction.

In general, (1) when the reaction medium is an appropriate form of carbon dioxide, it is usually preferred to conduct the reaction at temperatures in the range of 20°–80° C.; and it is sometimes even more preferred to have the temperatures in the range of 20°–40° C., most preferably 20°–30° C., and (2) when an appropriate form of another normally gaseous material is used, it is preferred to employ one which permits the reaction to be conducted at temperatures not higher than 80° C., preferably at temperatures not higher than 60° C.

The reaction medium is used in solvent amounts which, if desired, may be only the minimum required to keep the reaction mixture stirrable. However, unlike the process of Smith et al.-II, in which it is preferable to minimize the amount of solvent employed, there is no reason to minimize the amount of solvent used in the present process. Since the reaction medium can be easily vented from the reaction vessel by reducing the pressure at the end of the reaction, and the vented gas can be easily recycled, the economic advantages of the process are not lost when a considerable excess of the solvent is utilized. Thus, the amount of reaction medium employed is generally apt to be such that it constitutes about 10–75% by volume of the reaction mixture and the reaction medium/reactant weight ratio is at least 1/1.

As already mentioned, the process is conducted under a pressure sufficient to maintain the reaction medium in the desired state, but the pressure is not otherwise critical. Ordinarily, however, it is desirable to use an amount of pressure consistent with conducting an economical process, usually a pressure in the range of about 4.9–8.5 MPa.

After completion of the reaction, the system is vented to remove the reaction medium, and the amine oxide product is recovered from the reaction vessel. Any water remaining in the product may be removed by conventional means, if desired. However, except when the less concentrated hydrogen peroxides have been employed, there is generally no more than a negligible amount of water present in the product, and drying therefore is usually unnecessary.

The invention is advantageous in that it provides an economical means of preparing amine oxides which can be used in the preparation of powdered compositions, such as dry laundry detergent formulations, without first being subjected to after-treatments which could increase their cost and/or contaminate them with materials used in the after-treatments or with decomposition products formed during the after-treatments. It does not require the centrifugation and crystallization steps of Smith et al.-II and, in its preferred embodiments, requires no drying step either, so it permits the preparation of amine oxides at considerably less cost.

The following example is given to illustrate the invention and is not intended as a limitation thereof.

EXAMPLE

Part A

A mixture of 150 g of N-tetradecyldimethylamine and 0.5 g of diethylenetriaminepentaacetic acid was heated to 65° C., and 35 g of 70% hydrogen peroxide was added over a period of five minutes while maintaining the temperature. The reaction mixture was then stirred at 75° C. until gelation occurred after about 15 minutes, and the hot product was transferred to a storage vessel.

Part B

Part A was repeated twice to form additional product which was combined with the product of Part A.

Part C

A 2L 316SS Parr autoclave was charged with 347.5 g of a crude reaction mass which was composed of the combined products of Parts A and B and which was determined by NMR to be at the stage of 88% conversion. The autoclave was flushed three times with nitrogen and carbon dioxide. Then 1080 g of liquid carbon dioxide was added, and the reaction mixture was stirred and heated to 25° C., a temperature that was maintained for one hour. Exotherm was noted for the first 15 minutes, and the pressure went from 4.9 MPA at the beginning of the heatup to 25° C. to a peak pressure of about 8.5 MPa when the temperature reached 25° C. After the reaction conditions had been maintained for one hour, the autoclave was vented to the atmosphere. The product was a white solid powder which showed a 100% conversion to N-tetradecyldimethylamine oxide by NMR.

What is claimed is:

1. In a process for preparing an amine oxide by reacting a tert-amine with at least a stoichiometric amount of an aqueous hydrogen peroxide having a concentration of at least 50% by weight, the improvement which comprises conducting at least the latter part of the reaction in the presence as the reaction medium of a normally gaseous material which (a) has a critical temperature <160° C. and a critical pressure <12 MPa, (b) is in a liquefied, densified, or supercritical state in which it has a density of at least 0.1 g/cc, and (c) is present in an amount sufficient to maintain the reaction mixture stirrable throughout the reaction; said amount being such as to provide a reaction medium/reactant weight ratio of at least 1/1.

2. The process of claim 1 wherein the tert-amine is a compound corresponding to the formula RR'R"N in which R, R', and R" are independently selected from alkyl, hydroxyalkyl, cycloalkyl, and aralkyl groups containing up to 30 carbons and any two of those groups may form a non-aromatic heterocyclic group with the nitrogen.

3. The process of claim 2 wherein R is methyl, ethyl, or hydroxyethyl; R' is a primary alkyl group containing 6–24 carbons; and R" is independently selected from methyl, ethyl, hydroxyethyl, and primary alkyl groups containing 6–24 carbons.

4. The process of claim 3 wherein R and R" are independently selected from methyl, ethyl, and hydroxyethyl.

5. The process of claim 3 wherein R' and R" are independently selected from primary alkyl groups containing 6–24 carbons.

6. The process of claim 1 wherein the hydrogen peroxide has a concentration of at least about 70% by weight.

7. The process of claim 1 wherein the reaction medium is present throughout the reaction.

8. The process of claim 7 wherein the reaction is conducted by gradually adding the hydrogen peroxide to a solution of the tert-amine in the reaction medium and maintaining contact between the reactants until the reaction is substantially complete.

9. The process of claim 7 wherein the reaction is conducted by gradually adding separate streams of the tert-amine and the hydrogen peroxide to the reaction medium and maintaining contact between the reactants until the reaction is substantially complete.

10. The process of claim 7 wherein the reaction is conducted by gradually adding separate streams of the hydrogen peroxide and the reaction medium to the tert-amine and maintaining contact between the reactants until the reaction is substantially complete.

11. The process of claim 1 wherein the reaction medium is not added to the reaction mixture until it is needed to maintain the reaction mixture stirrable.

12. The process of claim 1 wherein the normally gaseous material is a gas which has a critical temperature of at least 0° C.

13. The process of claim 12 wherein the normally gaseous material has a critical temperature of 20°–50° C.

14. The process of claim 13 wherein the normally gaseous material is carbon dioxide.

15. The process of claim 1 conducted at a temperature and pressure below the critical temperature and pressure of the normally gaseous material so as to maintain the reaction medium as a liquefied gas.

16. The process of claim 1 conducted at a temperature and pressure above the critical temperature but below the critical pressure of the normally gaseous material so as to maintain the reaction medium as a densified gas.

17. The process of claim 1 conducted at a temperature and pressure above the critical temperature and pressure of the normally gaseous material so as to maintain the reaction medium as a supercritical fluid.

* * * * *